(12) United States Patent
Wilson et al.

(10) Patent No.: US 11,464,612 B2
(45) Date of Patent: Oct. 11, 2022

(54) DENTAL APPLIANCE POSITIONING CASE

(71) Applicant: NCASE INC, Las Vegas, NV (US)

(72) Inventors: Wesley P. Wilson, Huntsville, AL (US); Anthony Osibov, Las Vegas, NV (US)

(*) Notice: Subject to any disclaimer, the term of this patent is extended or adjusted under 35 U.S.C. 154(b) by 51 days.

(21) Appl. No.: 17/052,669

(22) PCT Filed: May 6, 2019

(86) PCT No.: PCT/US2019/030969
§ 371 (c)(1),
(2) Date: Nov. 3, 2020

(87) PCT Pub. No.: WO2019/213671
PCT Pub. Date: Nov. 7, 2019

(65) Prior Publication Data
US 2021/0236253 A1    Aug. 5, 2021

Related U.S. Application Data

(60) Provisional application No. 62/667,420, filed on May 4, 2018.

(51) Int. Cl.
*A61C 19/02* (2006.01)
*A45D 44/20* (2006.01)

(52) U.S. Cl.
CPC .............. *A61C 19/02* (2013.01); *A45D 44/20* (2013.01)

(58) Field of Classification Search
CPC .......... A45D 44/20; A61C 7/08; A61C 19/02; A61C 7/00; A61C 2202/00

USPC .................. 206/83, 369, 368, 63.5
See application file for complete search history.

(56) References Cited

U.S. PATENT DOCUMENTS

| | | | | |
|---|---|---|---|---|
| 2,196,566 A | * | 4/1940 | Sabattis | A61C 19/10 206/83 |
| 2,375,645 A | * | 5/1945 | Gordon | A45D 44/20 206/83 |
| 5,323,787 A | * | 6/1994 | Pratt | A61C 19/063 433/80 |
| 6,417,761 B1 | * | 7/2002 | Elliott | A61C 7/00 340/568.1 |
| 7,201,271 B1 | * | 4/2007 | Saad | A61C 17/036 206/63.5 |
| 8,657,108 B2 | * | 2/2014 | Nihei | A61C 19/02 206/63.5 |
| 10,441,395 B2 | * | 10/2019 | Mah | A61C 19/05 |
| 2004/0244805 A1 | * | 12/2004 | Cook | B65D 43/164 128/859 |
| 2008/0283422 A1 | * | 11/2008 | Jansheski | B65D 43/164 206/63.5 |
| 2010/0181214 A1 | * | 7/2010 | Brown | A61C 19/02 206/557 |
| 2013/0180870 A1 | * | 7/2013 | Nihei | A61C 19/02 206/63.5 |

(Continued)

*Primary Examiner* — Chun Hoi Cheung
(74) *Attorney, Agent, or Firm* — Charmasson, Buchaca + Leach, LLP

(57) ABSTRACT

A medical device storage device comprises a base, case insert, and insert hump. The insert hump is structured to position a medical device within a cavity formed at least partly by the case insert. At least a portion of a sensor is located within the insert hump and configured to detect a feature of the medical device. The feature of the medical device may correspond to an aspect of a treatment plan.

19 Claims, 13 Drawing Sheets

(56) References Cited

U.S. PATENT DOCUMENTS

| | | | |
|---|---|---|---|
| 2015/0136624 A1* | 5/2015 | Konig | A46B 15/0091 |
| | | | 206/63.5 |
| 2016/0100924 A1* | 4/2016 | Wilson | A45D 44/20 |
| | | | 206/63.5 |
| 2019/0110746 A1* | 4/2019 | Dau | A61B 5/02055 |

* cited by examiner

DENTAL APPLIANCE POSITIONING CASE

CROSS-REFERENCE TO RELATED APPLICATION(S)

This patent application is a PCT international application claiming priority to U.S. provisional application No. 62/667,420, the contents of which are herein incorporated by reference.

TECHNICAL FIELD

This patent application relates to the field of dental appliance cases. More specifically, this application relates to embodiments of dental appliance cases structured to position a dental appliance.

BACKGROUND

As more emphasis is being placed on dental concerns of a patient, the dental industry has continued to develop more appropriate dental appliance. In some situations, it is desirable to develop and utilize a removable dental appliance. Such dental appliances may include dentures, removable retainers, and other dental appliances.

If a dental appliance is removable, there is a possibility that the patient may lose the dental appliance, may forget to reinsert the dental appliance, or may fail to adhere to other aspects of a dental treatment plan. Accordingly, it may be desirable to provide the patient with the methods and tools that they need in order to properly adhere to the desired aspects of a dental treatment plan and to fully comply with the dental treatment plan.

SUMMARY

In one embodiment, a medical device storage case may comprise a base. A case insert may be connected to the base. An insert hump, connected to the case insert, may be structured to position a medical device within a cavity at least partially formed by the case insert. At least a portion of a sensor may be located within the insert hump and may be configured to detect a feature of the medical device.

In another embodiment, a medical device storage case may comprise a base. A case insert may be connected to the base. A first latitudinal insert hump may be connected to the case insert. A second latitudinal insert hump may also be connected to the case insert. A first portion of a sensor may be located within the first latitudinal insert hump and a second portion of the sensor may be located within the second latitudinal insert hump. The portions of the sensor may be configured to detect a feature of a medical device positioned between the first and second latitudinal insert humps.

DETAILED DESCRIPTION

In some circumstances, it is desirable for a patient to fully comply with a dental treatment plan. In order to comply with a dental treatment plan, the dental treatment plan may include one or more aspect of the dental treatment plan that needs to be adhered to by a certain level. However, it is not always easy or accurate to rely on a patient's memory and honesty. Accordingly, it may be beneficial for the patient to utilize a device that determines and tracks adherence and compliance with a dental treatment plan.

Figure 1:
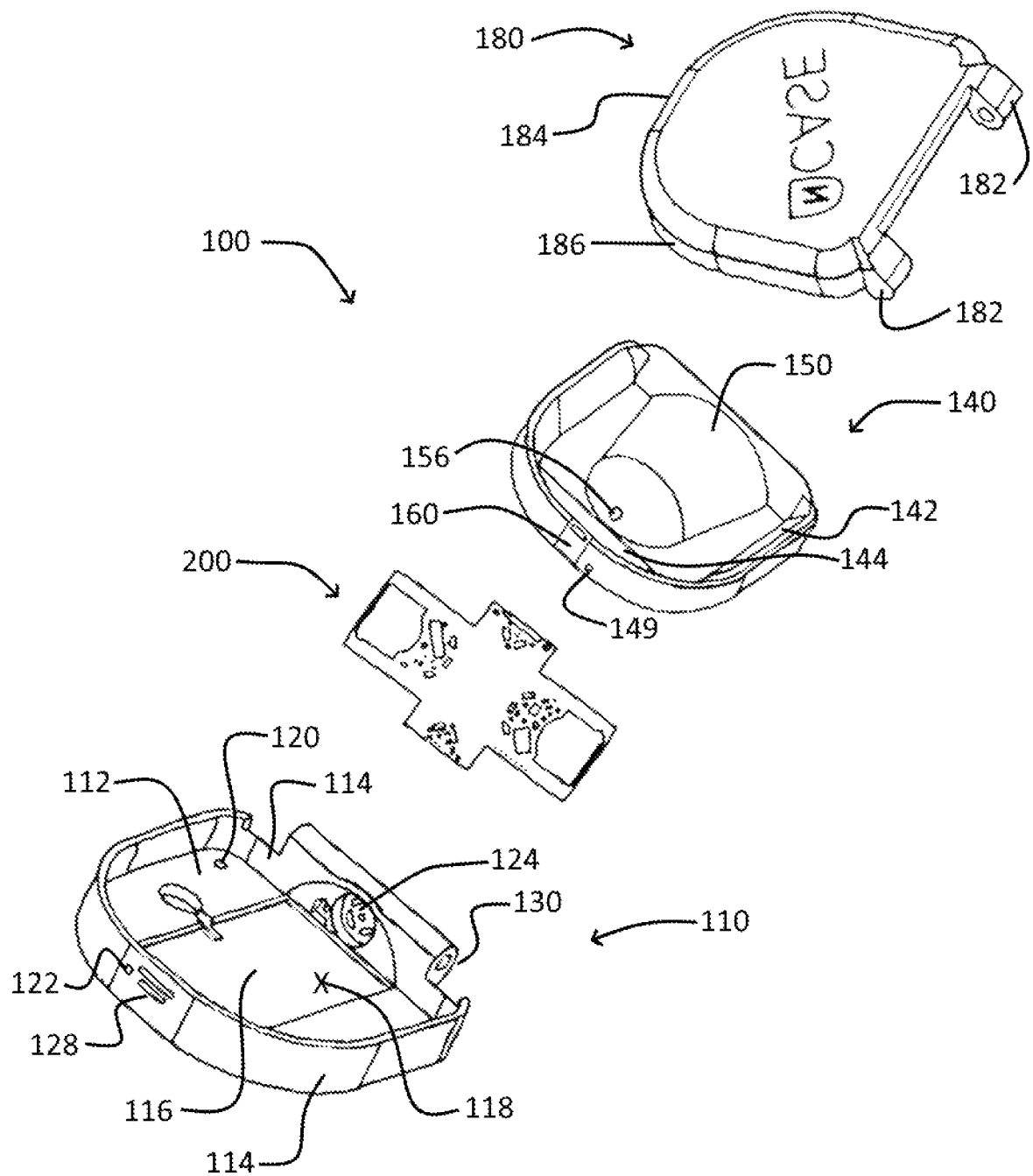
FIG. 1 depicts an embodiment of an exploded view of a dental appliance case.

FIG. 1 depicts an embodiment of a perspective view of a dental appliance case configured to determine and/or track compliance with and/or adhere to aspects of a dental treatment plan, or related data. The dental appliance case 100 may include a base 110 and a lid 180. Within a cavity formed by the base 110 and the lid 180, an insert 140 (embodiments depicted in other FIGs., such as FIG. 3) may be positioned. However, in some embodiments, the insert 140 may be integrally formed with other components, for example the base 110 or the lid 180.

Figure 2:
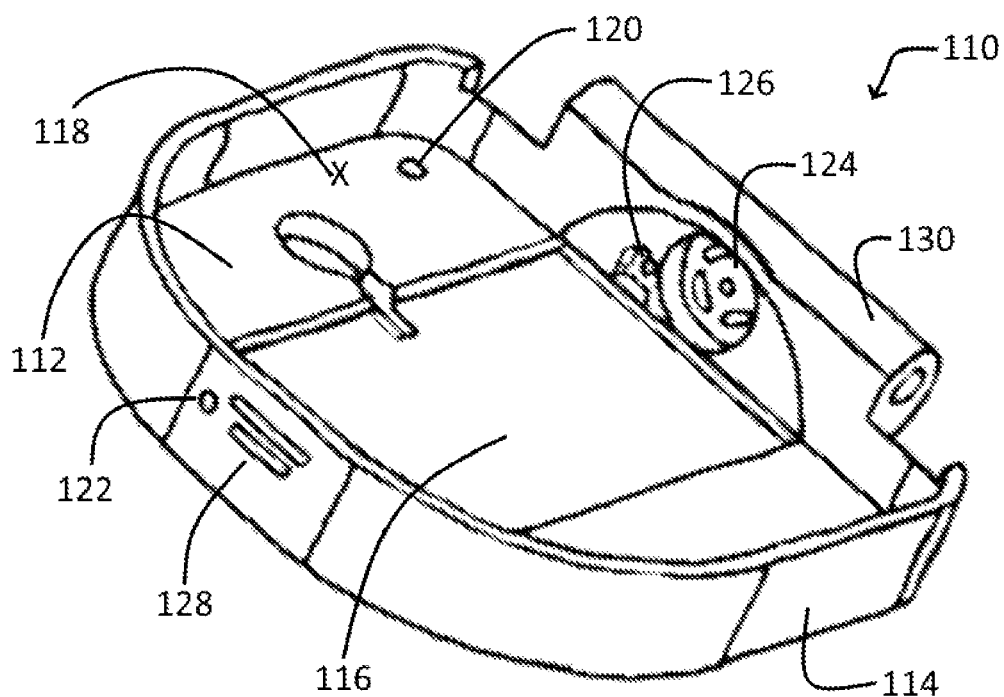
FIG. 2 depicts a top perspective view of an embodiment of a base of a dental appliance case.
Figure 3:
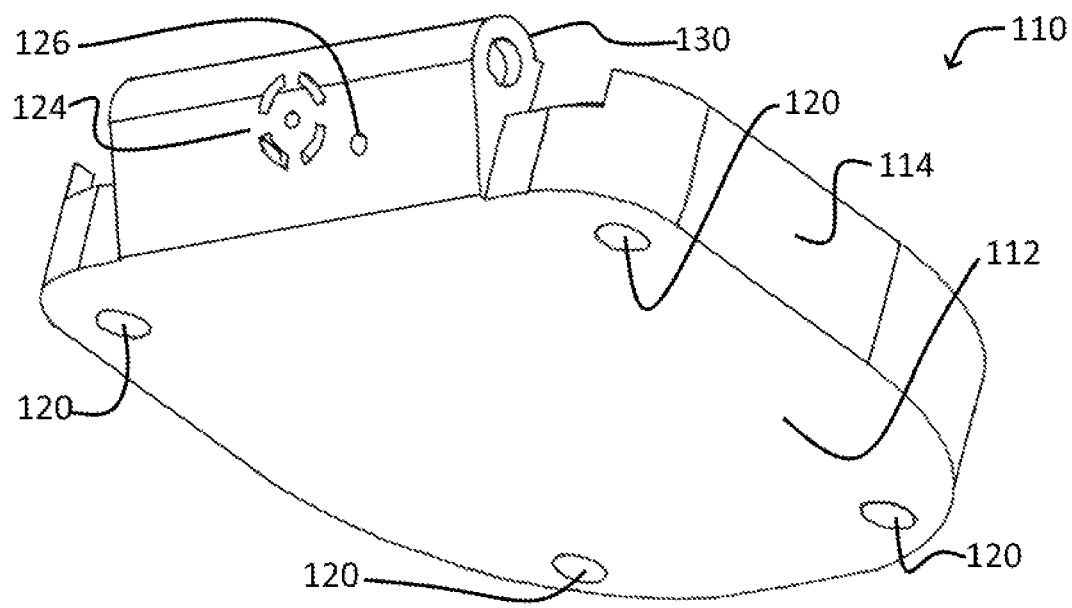
FIG. 3 depicts a bottom perspective view of an embodiment of a base of a dental appliance case.

FIGS. 2 and 3 respectfully depict a top and bottom perspective view of an embodiment of the base 110 of the dental appliance case 100. The base 110 may comprise a floor 112 abutted by one or more wall 114. In this embodiment, the wall 112 comprises both straight and curved portions. The general curvature of the wall 112 may generally follow the general curvature of a patient's teeth line, for instance an arch shape.

In some embodiments, the base 110 of the dental appliance case 110 may be structured to merely consist of a floor 112. More specifically, the base may not comprise one or more wall 114. Instead, a side wall of the dental appliance case 100 may be formed from a side wall of the case insert 140, which will be described in greater detail below.

Figure 4:
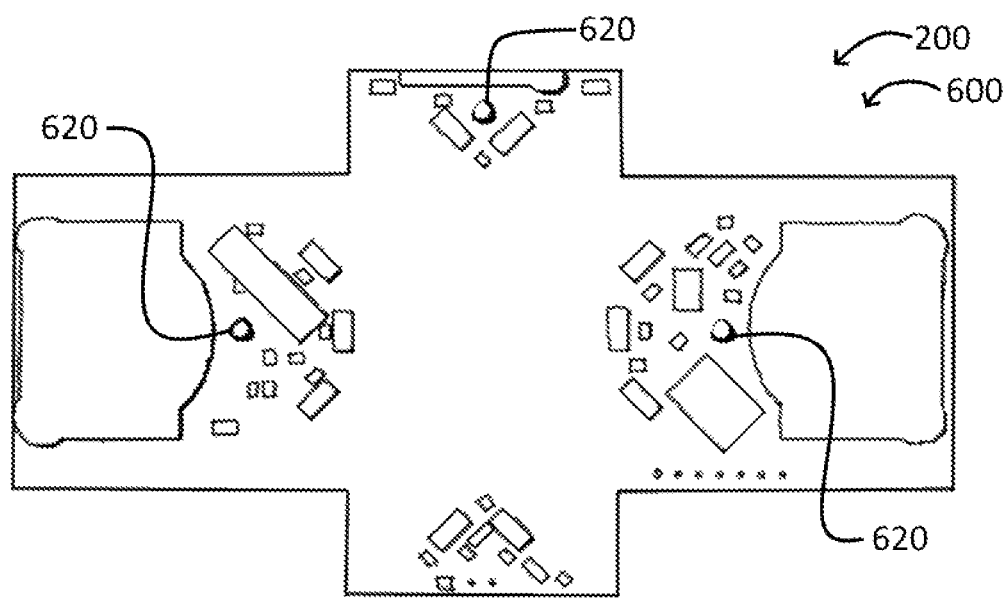
FIG. 4 depicts an upper view of an embodiment of a Printed Circuit Board (PCB).

The floor 112 and/or wall 114 may include one or more indentation 116 shaped for at least partially receiving electronic components, such as the printed circuit board (PCB) 200 depicted in FIG. 4. The floor 112 and/or the wall 114 may further comprise a cavity 118 structured to receive an insert 140. The floor 112 and/or the wall 114 may still further comprise a base mounting aperture 120. The base mounting aperture 120 may be structured and positioned within the floor 112 and/or wall 114 so as to properly align and secure the PCB 200 within the cavity formed by the floor 112 and/or wall 114.

The floor 112 and/or wall 114 may include other indentations, cavities, and/or apertures that aid with the functionality of the dental appliance case 100. For instance, the floor 112 and/or wall 114 may comprise a visual notification aperture 122. The visual notification aperture 122 may be structured to allow a patient to view information corresponding to the dental appliance and/or dental treatment plan. For instance, the visual notification aperture 122 may be structured to allow the light from a light emitting diode to shine through. Based on one or more feature of the light emitting diode, such as the color, duration, frequency, etc., the patient may be able to comprehend the information attempting to be conveyed, even without opening the lid 180 of the dental appliance case 100. For instance, if the light emitting diode is blinking red, then the patient may comprehend that the dental appliance has been within the case 100 for too long of a period of time. However, if the light emitting diode is a solid green, then the patient may comprehend that the patient has worn the dental appliance for enough time to adhere to the wear time aspect of the dental treatment plan. Of course, information may be visually displayed in any number of fashions.

In some embodiments, the visual notification aperture 122 may alternatively or additionally be positioned in other locations of the dental appliance case 100. For instance, the visual notification aperture 122 may be positioned within the lid 180 of the dental appliance case 100. With such positioning, a patient may be able to more conveniently view the information that is being provided by the dental appliance case 100. For instance, the visual notification aperture 122 may have a visual display positioned within. Such a visual display may be able to provide information that is easier to comprehend by a patient. Any wires that are needed to provide data and/or power to the notification device may be run through a hinge 130. Alternatively, the information may be provided by a device that is not located within the visual notification aperture 122. For instance, the visual notification device may be positioned within the insert hump 150 and/or on the PCB 200. An aperture may be provided within the insert hump 150 and be positioned to align with the visual notification aperture 122.

The floor 112 and/or wall 114 may further comprise an auditory notification aperture 124. The auditory notification aperture 124 may comprise one or more opening. The auditory notification aperture 124 may be aligned with an auditory notification device located within the dental appliance case. For instance, the auditory notification aperture 124 may be aligned with a speaker, piezoelectric device, or other sound emitting device attached to the PCB 200. In the depicted embodiment, the auditory notification aperture 124 is located in a back wall 114 of the dental appliance case 100, although other locations may be more preferable in other embodiments. Based in the auditory notification that at least partially travels through the auditory notification aperture 124, a patient may be able to comprehend information being transmitted by the dental appliance case 100. For instance, the auditory information may correspond to a feature of the dental appliance or may relate to one or more aspect of the dental treatment plan or compliance with such treatment plan.

The floor 112 and/or wall 114 may further comprise one or more input aperture 126. The input aperture 126 may be structured to allow a user to input information to the dental appliance case 100 through the input aperture 126. Such information can be input digitally or physically. For instance, information corresponding to a dental treatment plan may be input using a cable connected to a receiver that is at least partially located within the input aperture 126 or by passing a portion of the cable through the input aperture 126. As another example, a user may pass a thin object, such as a pin or paper clip, through the input aperture 126 to physically actuate a button located within the dental appliance case, such as a reset button. Based on the user input through the input aperture 126, various features and/or functionalities of the dental appliance case may be updated, changed, erased, or newly created.

The floor 112 and/or wall 114 may further comprise a locking mechanism 128. The locking mechanism 128 may be structured to aid in temporarily maintaining the position of the lid 180 and the base 110. For instance, the locking mechanism 128 may temporarily maintain the lid 180 and the base 110 in a closed position. The locking mechanism 128 may be structured in any fashion that temporarily maintains the lid 180 and base 110 in a desirable position. In one embodiment, the locking mechanism 128 comprises a push tab located in the wall 114 of the dental appliance case 100. The push tab may engage the lid 180 when brought together so as to keep the lid 180 secured to the base 110, thereby preventing any contents within the dental appliance case 100 from escaping. In another embodiment, the locking mechanism 128 may not directly contact the lid locking mechanism 184. Instead, the locking mechanism may act on the locking tab 160 of the case insert 140 to disengage the locking tab 160 from the lid locking mechanism 184.

The floor 112 and/or wall 114 may further comprise a base hinge 130. For instance, in one embodiment, the base hinge 130 is integrally formed with a wall 114 of the dental appliance case. The base hinge 130 may be engaged with the lid hinge 182 so that the lid 180 may be moved with respect to the base 110. For instance, the engaged base hinge 130 and lid hinge 182 may allow the lid 180 to pivot about a wall 114 of the dental appliance case 100. The base hinge 130 and the lid hinge 182 may assist the locking mechanism 128 with maintaining a locked positioned.

The base hinge 130 and the lid hinge 182 may be integrally formed in certain embodiments. For instance, they may be integrally formed to form a living hinge. Other separate or integrated hinges may be selected and implemented based on other embodiments of the dental appliance case 100. However, in other embodiments, separate or integrated hinges may not be used. Instead, they can be absent or they can be implemented as an additional locking mechanism 128.

Figure 5:
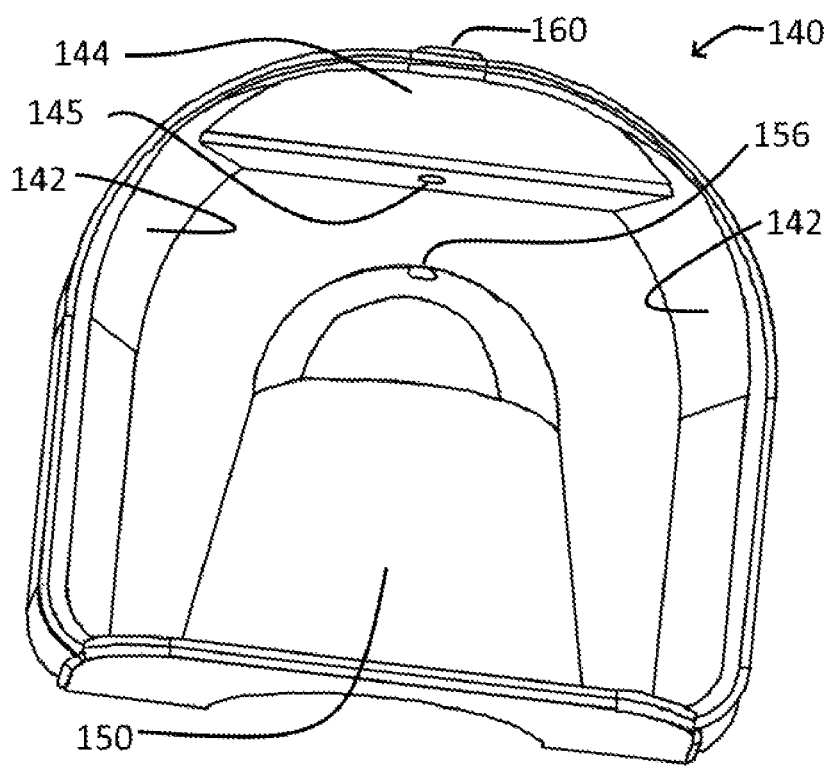
FIG. 5 depicts a top perspective view of an embodiment of an insert of a dental appliance case.
Figure 6:
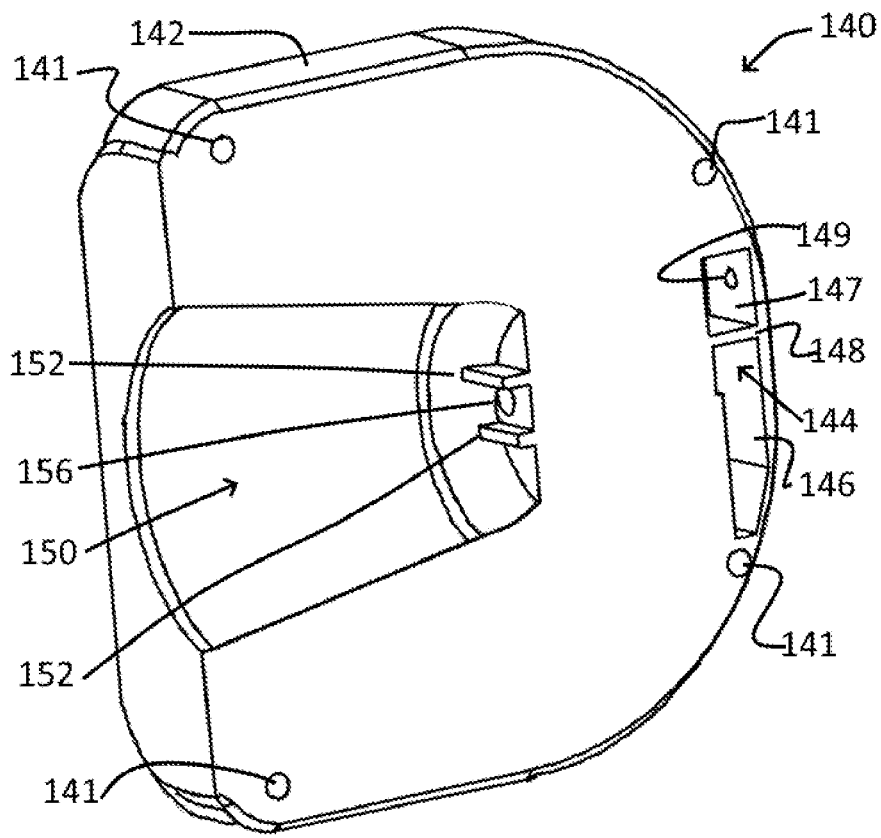
FIG. 6 depicts a bottom perspective view of an embodiment of an insert of a dental appliance case.
Figure 7:
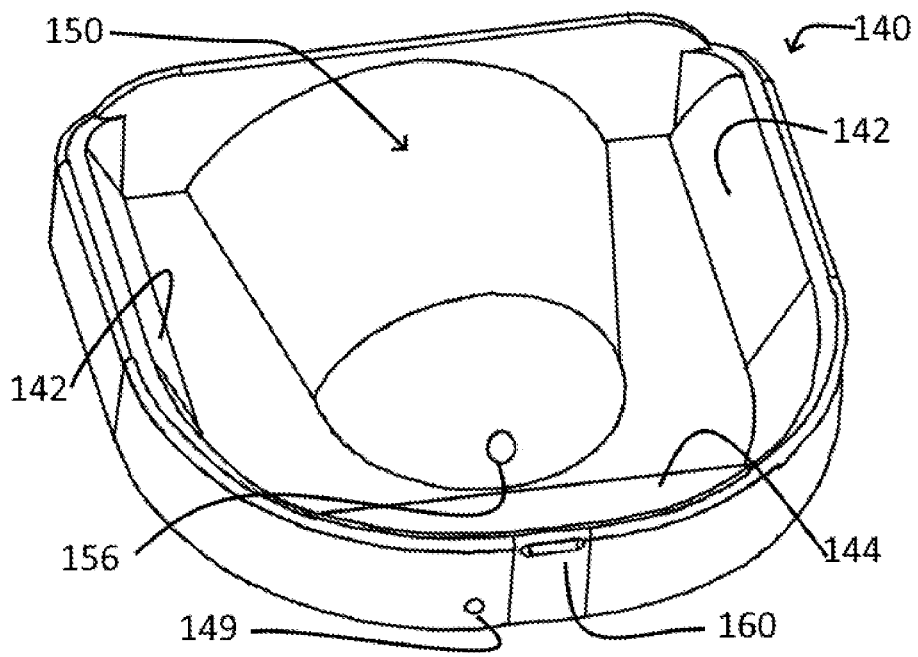
FIG. 7 depicts a top perspective view of an embodiment of an insert of a dental appliance case.

FIGS. 5-7 depict perspective views of embodiments of an insert of the dental appliance case. For instance, case insert 140 may be structured to fit within the base 110 and/or lid 180. For example, the case insert 140 may be structured such that it can fit within the wall(s) 114 of the base 110 and be able to be positioned on top of the floor 112 and/or PCB 200. The case insert 140 may further be structured such that at least a portion fits within the lid 180.

The case insert 140 may comprise one or more insert wall 142. In some embodiments, the one or more insert wall 142 may be partially or fully sloped. The amount, angle, and/or shape of the slope may be determined based on one or more parameter. For instance, the insert wall 142 may be sloped in a certain fashion to aid in a more preferential alignment of a dental appliance within the dental appliance case 100. For example, the sloped insert wall 142 may engage at least a portion of the dental appliance. By engaging at least a portion of the dental appliance, the insert wall 142 may aid in guiding the dental appliance into a position that sensors are better able to obtain data related to aspects of a dental treatment plan, for instance a wear time. That is, the insert wall 142 may guide the dental appliance towards a bottom central location of the case insert 140.

However, the precise dimensions of the dental appliance may not be known at the time of manufacturing the dental appliance case. To compensate for such potentially unknown variables, the insert wall 142 may be positioned such that the sloped features of the insert wall 142 compensate for the potential differences. For example, it may be anticipated that there will be a large variance in the size of the dental appliance that may be stored in the dental appliance case 100, such as if both child and adult dental appliances are anticipated to be stored. In such a situation, the insert wall 142 may be structured to have a smaller or more gradual incline. With such a sloping characteristic, a wide variety of dental appliance widths could be positioned more appropriately. In some situations, this may mean positioning the dental appliance towards the center of the dental appliance case 100. Since a gradual incline is being implemented, differing widths of dental appliances may be positioned towards the center of the case, in a horizontal plane, while not substantially affecting the positioning of the dental appliance in a vertical plane. This may have the benefit of better positioning of the sensor(s). This may result in more accurate data and determinations from the sensor(s) and/or reducing the number of sensors that are needed to obtain such data for determinations.

However, if the anticipated differences of the dimensions of the dental appliance are anticipated to be small, it may be more desirable to increase the angle of the slope of the insert wall 142. This may allow for proper alignment of the dental appliance, while reducing the dimensions of the case insert 140 and dental appliance case 100. That is, since the angle of the slope of the insert wall 142 is larger, the effective thickness of the insert wall 142 can be reduced. The reduced wall thickness may result in reducing the dimensions of the case insert 140 and the dental appliance case 100.

In some embodiments, at least a portion of a sensor may be located in one or more insert wall 140. The positioning of at least a portion of a sensor in one or more insert wall 140 may be instead of or in addition to sensor(s) located in insert hump 150.

The case insert 140 may comprise a sensor housing 144. The sensor housing may be positioned along one or more wall 142 of the case insert 140. In some embodiments, it is preferable that the sensor housing 144 be positioned across from the hump sensor opening 156. However, depending on the type of sensor(s) that are present within the dental appliance case 100, the sensor housing 144 may be located in a different position. However, it is preferable that the sensor housing 144 be positioned such that any sensor(s) within the sensor housing 144 may be able to function as intended.

In some embodiments, the sensor housing 144 may be positioned towards one end of the case insert 140 and may be positioned away from a distal end of an insert hump 150. In such a position, the sensor housing 144 may aid in maintaining proper positioning of a dental appliance. For example, the spacing between the sensor housing 144 and the distal end of the insert hump 150 may be positioned relatively close together. That is, they are positioned such that there is little extra room in the gap when the dental appliance is located within the gap. This may reduce the amount of variance that the dental appliance will be located along one axis of a horizontal plane of the case insert 140. With a more predictable positioning, the sensor(s) located within the dental appliance case may be able to obtain better data, thereby assisting with more accurate determinations of compliance and/or adherence to aspect(s) of a dental treatment plan.

The sensor housing 144 may comprise at least one sensor cavity 146 and/or at least one notification cavity 147. The sensor cavity 146 may be structured to receive at least a portion of a sensor, and the notification cavity 147 may be structured to receive at least a portion of a notification device. A dividing wall 148 may be positioned between one or more of the cavities of the sensor housing 144. The dividing wall 148 may be structured to reduce interference caused by the notification device located in the notification cavity 147 with the sensor(s) located in the sensor cavity 146, and/or vis versa.

The sensor housing 144 may also comprise a notification aperture 149. The notification aperture 149 may be positioned to align with the visual notification aperture 122, when the base 110 and the case insert 140 are mated. With such positioning, a notification device located in the notification cavity 147 will be visible by the patient, via the notification aperture 149 and the visual notification aperture 122.

The sensor housing 144 may comprise one or more housing sensor aperture 145. The housing sensor aperture 145 may be positioned to align with at least a part of one or more sensor for detecting an aspect of the dental treatment plan. However, in some circumstances, the housing sensor aperture 145 may not be aligned with the sensor. The relative positioning of the sensor and the housing sensor aperture 145 may depend on the positioning that results in the most accurate reading of the sensor.

The case insert 140 may further comprise one or more insert hump 150. The insert hump 150 may be positioned so as to be aligned with one or more insert wall 142. The insert hump 150 may extend from one of the insert wall 142 towards an opposite side of or opposing insert wall insert wall 142. However, the distal end of the insert hump 150 is positioned so as to not directly contact the relevant portion of the opposite side or opposing distal wall 142. The distal end of the insert hump 150 may also be positioned such that it does not directly contact the sensor housing 144. A proximal end of the insert hump 150 may directly contact one or more insert wall 142.

In some embodiments, the distance between the distal end of the insert hump 150 and the sensor housing 144 is related to the size of the dental appliance anticipated to be stored in the dental appliance case 100. In one example, the distance between the distal end of the insert hump 150 and the sensor housing 144 may be the size of an incisors portion of the dental appliance that that is anticipated to be stored in the dental appliance case. In one example, the distance between the distal end of the insert hump 150 and the sensor housing 144 may be closer towards a lower portion of the distal end of the insert hump 150 and a lower portion of the sensor housing 144, than between an upper portion of the distal end of the insert hump 150 and an upper portion of the sensor housing 144. Such a relative positioning may be implemented when the incisor portion of the dental appliance generally corresponds to the anticipated incisor shape of a patient. More specifically, a patient's incisors may generally taper towards a distal end, away from the gum line. To further follow the general shape of a patient's incisors, the sensor housing 144 may have a surface that is relatively perpendicular to the floor of the case insert 140, while the distal end of the insert hump 150 may have a sloped surface, generally sloping towards the proximal end of the insert hump 150.

In some embodiments, the width of the insert hump 150 may be generally consistent along its length. However, the width of the distal end of the insert hump 150 may taper towards the distal end. In other embodiments, the width of the insert hump 150 may generally become narrower from the proximal end of the insert hump 150 to the distal end.

In some embodiments, the height of the insert hump 150 may be generally consistent along its length. However, the height of the distal end of the insert hump 150 may taper towards distal end. In other embodiments, the height of the insert hump 150 may generally become shorter from the proximal end of the insert hump 150 to the distal end.

In some embodiments at least a portion of the height of the insert hump 150 may be higher than at least one insert wall 142. For instance, a proximal end of the insert hump 150 may be higher than a side insert wall 142. Such positioning allows for a higher height of at least a portion of the insert hump 150.

In some embodiments at least a portion of the height of the insert hump 150 may be lower than at least one insert wall 142. For instance, a proximal end of the insert hump 150 may be lower than a back insert wall 142. Such a positioning allows the insert wall 142 to provide beneficial features not possible with the other insert walls 142, such as increased support of other components such as the hinge 130, while not exposing the opening formed by the shape of the hump, for instance by exposing the cavity through the proximal side of the insert hump 150.

In some embodiments, the insert hump 150 may generally have a semi-cylindrical or semi-conical-frustrum shape. The distal end of the insert hump 150 may have a different shape than the rest of the insert hump 150. For instance, the distal end of the insert hump 150 may generally have a tapered shape, for instance a half-spherical-cap.

In some embodiment, the general shape of the insert hump 150 may be structured such that electronic components physically and/or electrically connected to the PCB 200 may be housed within the insert hump 150. For instance, some electronic components may be physically connected to an upper surface of the PCB 200. The relative positioning of the electronic components and the insert hump 150 may be such that the electronic components are positioned within the cavity formed by the insert hump 150. Since the electronic components do not all have the same size, the shape of the insert hump 150 and the positioning of the electronic components on the PCB may be such that the taller electronic components are positioned on the PCB 200 such that they are within a taller portion of the insert hump 150. For instance, if the power source of the dental appliance case 100 is taller than the a resistor of the dental appliance case, the power source component may be positioned on the PCB 200 such that it aligns with the proximal end of the insert hump 150, given that the proximal end is taller than other portions of the insert hump 150. Since the insert hump 150 has a height and width so as to form a sizable cavity and since the electronic components positioned on the PCB 200 so as to correspond to the shape of the insert hump 150, the overall height of the dental appliance case 100 may be reduced.

The insert hump 150 may further comprise one or more hump sensor aperture 156. The hump sensor aperture 156 may be positioned along the insert hump 150 so as to align with the housing sensor aperture 145. The diameter of the hump sensor aperture 156 may correspond to that which would result in the most accurate reading of the corresponding sensor. In some embodiments, the hump sensor aperture 156 is located towards a distal end of the insert hump 150. One or more hump sensor aperture 156 may be located in another portion of the insert hump 150. The numbering and positioning of the hump sensor aperture 156 may depend on the number and types of sensors being used by the dental appliance caser 100.

The insert hump 150 may further comprise a hump sensor shield 152. The hump sensor shield 152 may be positioned towards a distal end of the insert hump 150 and within the cavity formed by the insert hump 150. The hump sensor shield 152 may be positioned so as to straddle the hump sensor aperture 156. The hump sensor shield 152 may be positioned to align or partly surround one or more sensor positioned within the cavity of the insert hump 150. The hump sensor shield 152 may be structured to minimize the extraneous sensor data coming from non-corresponding sensors and/or reduce noise. The sizing of the hump sensor shield 152 may also be so as to allow more favorable positioning of sensors within the cavity of the insert hump 150. For instance, the hump sensor shield 152 may have longer walls so as to allow a sensor to be positioned within the cavity of the insert hump 150 but further away from the hump sensor aperture 156. In some circumstances, such positioning of the sensor allows for more accurate sensor readings.

In some embodiments, one or more sensor aperture may be positioned within the insert wall 142. The one or more wall sensor aperture may correspond to one or more hump sensor aperture 152. A single wall sensor aperture may correspond to a single hump sensor aperture 156, or vis versa. The wall sensor aperture(s) and the hump sensor aperture(s) 156 may align with each other or may be misaligned. With additional wall sensor aperture(s) and/or hump sensor aperture(s) 156, more accurate and/or additional data may be collected regarding aspects of the dental treatment plan. Accordingly, a more accurate determination of compliance to a dental treatment plan may be made.

In some embodiments, the slope of the insert hump 150 and the insert wall 142 may work in conjunction with each other to appropriately position a dental appliance within the dental appliance case 100. For example, the slope of the insert hump 150, and/or the slope of the distal end of the insert hump 150, may be structured such that the positioning of the dental appliance is made appropriate for smaller sized dental appliances, even if the dental appliance does not contact the insert wall 142. However, the slope of the insert wall 142 may be structured such that a larger dental appliance is appropriately positioned within the dental appliance case 100, even if it does not contact the insert hump 150. In some situations, it may be appropriate to ensure the vertical positioning of the dental appliance aligns with the sensor housing aperture 145 and/or the hump sensor aperture 156. Since the slopes of the insert wall 142 and the insert hump 150 may be different, different sized dental appliances may be stored using the same dental appliance case, without substantially negatively affecting the data collected by the sensors.

The case insert 140 may further comprise one or more insert mounting aperture 141. The insert mounting aperture 141 may be positioned in a bottom surface of the case insert 140. The insert mounting aperture 141 may be positioned so as to align with the base mounting aperture 120, such that mounting hardware may pass through the base mounting aperture 120 and into or through the insert mounting aperture 141. The mounting hardware in conjunction with the base mounting aperture 120 and the insert mounting aperture 141 may function to maintain the relative positioning of the base 110 and the case insert 140. If the mounting hardware is structured to be removable, then the various components of the dental appliance case 100 may be replaced. For example, the mounting hardware could include a screw, which would allow the base 110, PCB 200, and case insert 140 to be decoupled so as to allow for replacing or repairing these parts or other components.

The case insert 140 may further comprise a locking tab 160. The locking tab 160 may be positioned so as to align with the locking mechanism 128 of the base 110. The locking tab 160 may work in conjunction with the locking mechanism 128 to assist with maintaining the relative position of the base 110 and the lid 180. In some embodiments, the locking tab 160 may engage a lid locking mechanism 184. The locking tab 160 may be disengaged from the lid locking mechanism 184 when a lateral force is acted on the locking tab 160. Although a push tab type of locking mechanism has been described, other locking mechanisms may be used for maintaining the relative positioning of the base 110 and lid 180, which would result in differing structures. However, in the interest of conciseness, such well known locking mechanisms will not be described.

In some embodiments, the insert hump 150 may be integrally formed with the case insert 140. However, in other embodiments, at least a portion of the insert hump 150 may not be so integrally formed. For example, a distal end of the insert hump 150 may not be integrally formed with the case insert 140. Instead, the distal end of the insert hump 150 may be adhered to the case insert 140. By not integrally forming the distal end of the insert hump 150 with the case insert 140, the distal end of the insert hump 150 may be adhered to the case insert 140 at a later time. This may allow for the size of the distal end of the insert hump 150 to be selected based on the particular dental appliance that is anticipated to be stored in the dental appliance case 100. For instance, the width, height, slope, etc. of the distal end of the insert hump 150 may be adjusted without the need to manufacture numerous different versions of the case insert 140. Other portions of the insert hump 150 may not be integrally formed with the case insert 140 so as to allow adjustments depending on the stored dental appliance.

In some embodiments, the insert wall 142 of the case insert 140 may function as the side wall of the dental appliance case. More specifically, the insert wall 142 may extend below the floor of the case insert 140. With the insert wall 142 extending below the floor, a cavity will be formed to house at least a part of the PCB 200. Electronic components electrically connected to the PCB 200 may be positioned within the insert hump 160, sensor housing 144, and/or within one or more insert wall 142. In such embodiments, the base 110 may optionally comprise one or more cavity within the floor 112, and may optionally not comprise a wall 114. That is, the base 110 may be essentially formed of a flat plate, with or without cavities for housing electronic components electrically connected to the PCB 200. If the base 110 does not comprise a wall 114, or the wall is of insufficient height, the features previously discussed regarding the wall 114, such as the base hinge 130, auditory notification aperture 124, locking mechanism 128, etc., may be formed in the insert wall 142. One of the benefits of these embodiments is that the overall length and width of the case may be reduced.

Figure 8:
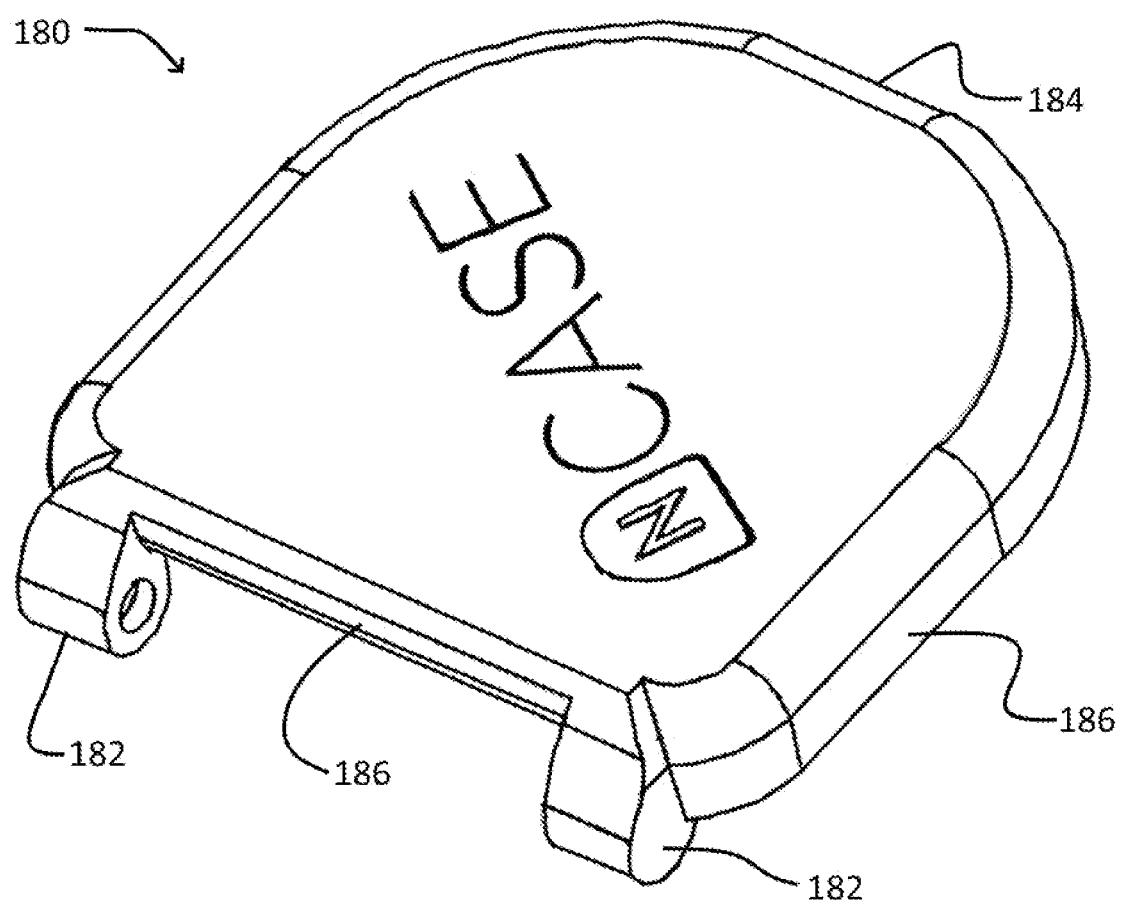
FIG. 8 depicts a top perspective view of an embodiment of a lid of a dental appliance case.

The dental appliance case 100 may further comprise a lid 180, a perspective view of an embodiment of which is depicted in FIG. 8. The lid 180 may be pivotally attached to the base 110 via the lid hinge 182 and the hinge 130 of the base 110. The lid 180 may further comprise a lid locking mechanism 184. The lid locking mechanism 184 may be positioned on an opposite side of the lid 180 than the lid hinge 182.

The lid 180 may further comprise one or more lid wall 186. At least a portion of the lid wall 186 may be structured to be longer than that of another portion or a separate lid wall 186. For instance, a side lid wall 186 may be positioned to be longer than a back lid wall 186. When the lid 180 and the base 110 are positioned such that the dental appliance case 100 is closed, the longer lid wall 186, or portion thereof, may extend past the top portion of the insert hump 150 and/or the dental appliance within the dental appliance case 100. That is, the insert hump 150 and/or dental appliance may extend into a cavity of the lid 180 when the dental appliance case 100 is closed. This structuring may allow for increased rigidity of the lid 180, for example due to the formed corner, while reducing the overall size of the dental appliance case 100.

In some embodiments, the base 110 may not comprise a wall 114. Instead, the base 110 may be essentially flat. If such a structure is implemented, the base 110 may still comprise one or more base mounting aperture 120 for aiding with maintaining the relative positioning of the base 110, PCB 200, and case insert 140. The base 110 may be structured to at least partially be positioned within a cavity formed in a lower portion of the case insert 140.

The material, color, texture, etc. of the case insert 140 and/or the lid 180 may be adjusted to improve the data obtained by the sensors. For instance, if an IR sensor is being used, it may be beneficial to form the case insert 140 and/or lid 180 of a dark material to increase the surface roughness of the inner surfaces. This may have such benefits as preventing outside IR light from entering the dental appliance case 100 and for reflection of IR light within the dental appliance case 100, both of which may lead to inaccurate readings. Data collected by the sensor(s) may be further improved by modifying other aspects of the material, color, texture, etc. of the case insert 140 and/or lid 180.

Figure 9:
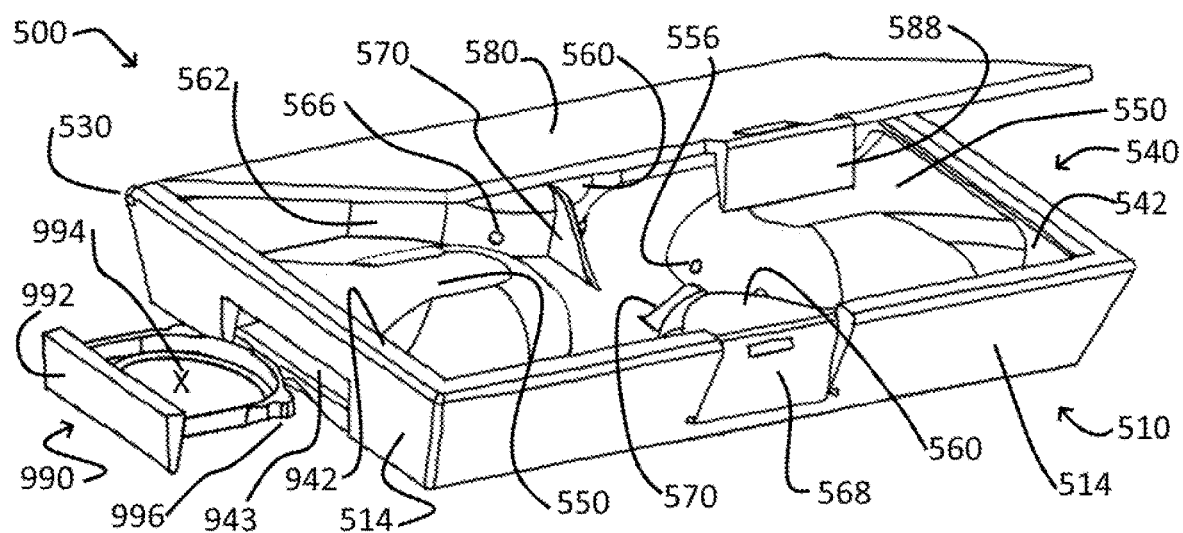
FIG. 9 depicts a front perspective view of an embodiment of a dental appliance case.

FIG. 9 depicts a perspective view of an embodiment of a dental appliance case comprising more than one insert hump. More specifically, the embodiments comprise a dental appliance case 500 that comprises two latitudinal insert humps 550 and two longitudinal insert humps 560. The dental appliance case 500 may comprise a base 510, a printed circuit board (PCB) 600, a case insert 540, and a lid 580.

Figure 10:
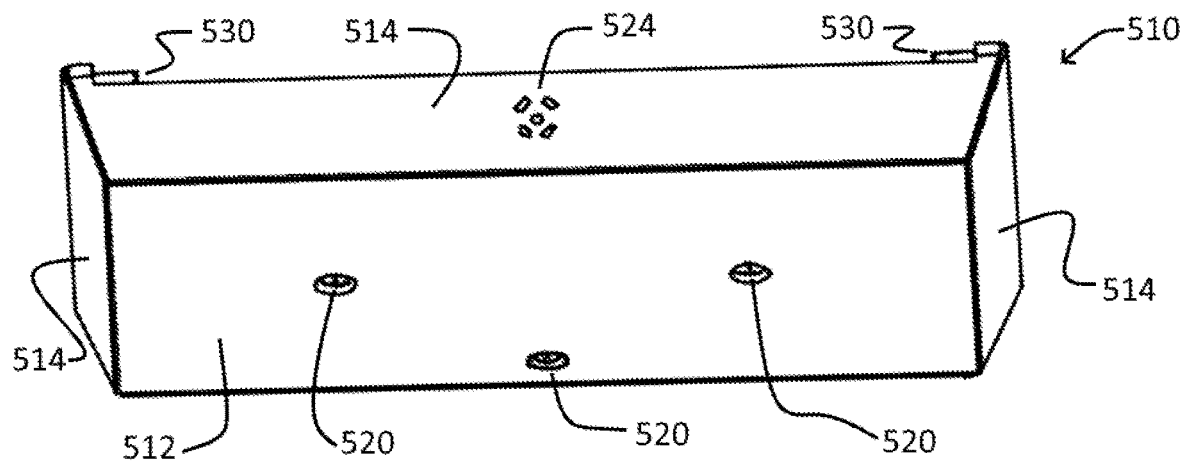
FIG. 10 depicts a bottom perspective view of an embodiment of a base of a dental appliance case.

FIG. 10 depicts a bottom perspective view of an embodiment of the base 510 of the dental appliance case 500. The base 510 may comprise one or more base wall 514. One or more base hinge 530 may be positioned towards one edge of the base wall 514. One or more base wall 514 may comprise an auditory notification aperture 524. The auditory notification aperture 524 may be positioned in the base wall 514 such that it aligns with an auditory notification providing electronic component electrically connected to the PCB 600. The one or more base wall 514 may contact a base floor 512 so as to form a cavity within the base. In some embodiments one or more of the base walls 514 may be essentially perpendicular to the base floor 512, while one or more of the other base walls 514 may be positioned at an angle other than perpendicular to the base floor 512.

The dental appliance case 500 may further comprise one or more base hinge 530. The base hinge 530 may engage with a corresponding lid hinge. The base hinge 530 and the lid hinge cooperatively work to form a hinge between the lid and base. That is, the hinges aid in allowing the lid 580 and base 530 to pivotally move with respect to each other. In some embodiments, other types of hinges may be used, or the hinges may be completely absent.

The base 510 may further comprise one or more base mounting aperture 520. The base mounting aperture 520 may be structured so as to allow a portion of mounting hardware to pass through. The mounting hardware may contact a portion of the base 510 and/or base mounting aperture 520, such as at a recces formed in the base 510 near the base mounting aperture 520. The base mounting aperture 520 may be positioned so as to align with the PCB mounting aperture 620 and the latitudinal insert mounting aperture 554 and/or the longitudinal insert mounting aperture 564.

Figure 11:
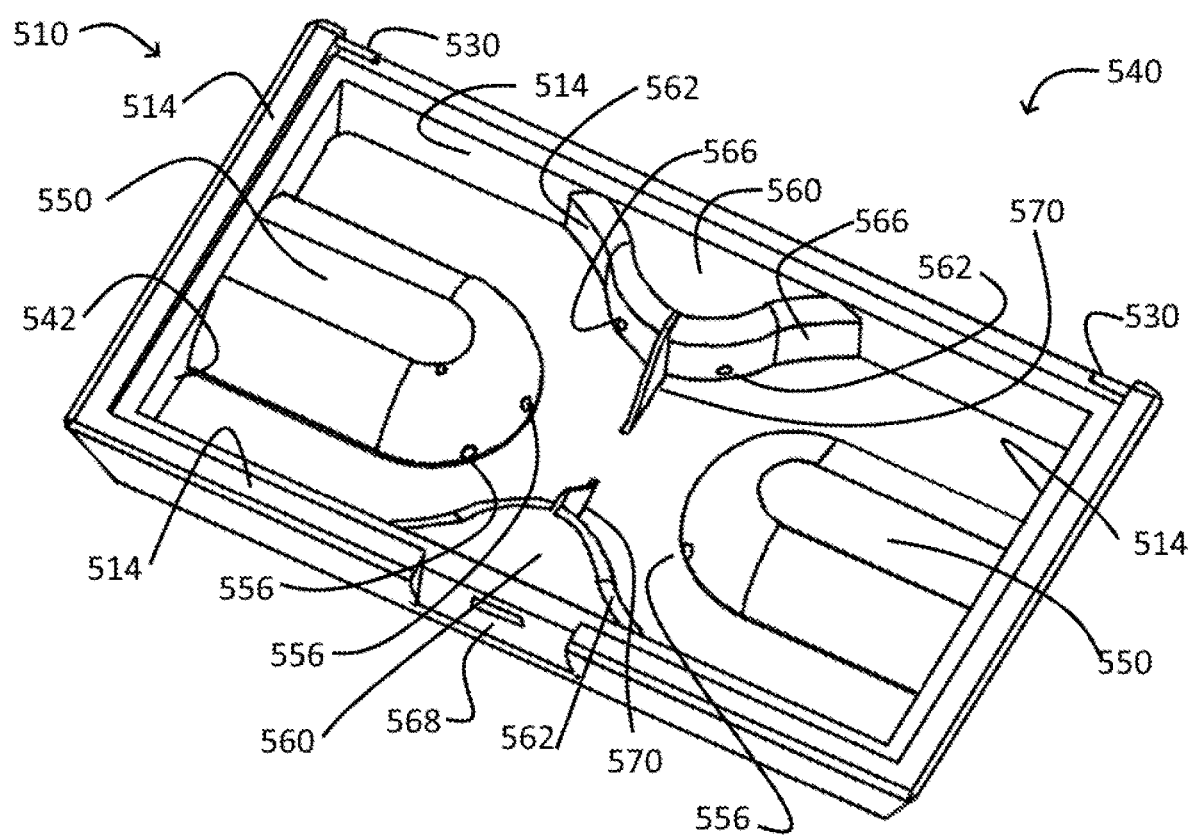
FIG. 11 depicts a top perspective view of an embodiment of a case insert and base of a dental appliance case.

FIG. 11 depicts a top perspective view of an embodiment of a case insert 540 and a base 510 of a dental appliance case 500. The case insert 540 may further comprise one or more insert locking mechanism 568. The insert locking mechanism 568 may engage the lid locking mechanism 588 to aid in temporarily maintaining the positioning of the lid 580 and the base 510. More specifically, the locking mechanisms may aid in maintaining the lid 580 in a closed position. In this embodiment, the lid 580 may be unlocked so as to pivot about the base hinge 530 and lid hinge to position the lid 580 in the open position. In this embodiment, unlocking may be accomplished by lifting the lid locking mechanism 588 so as to be disengaged from the insert locking mechanism 568. In some embodiments, different locking mechanisms may be used.

In some embodiments, a case insert 540 may be at least partially positioned within the cavity formed by the base wall(s) 514 and base floor 512. The case insert 540 may comprise a plurality of latitudinal insert humps 550 and/or a plurality of longitudinal insert humps 560. The latitudinal insert humps 550 may be positioned along a latitudinal direction of the case insert 540 and the longitudinal insert humps 560 may be positioned along a longitudinal direction of the case insert 540. Each of the latitudinal insert humps 550 and the longitudinal insert humps 560 may contact an insert wall 542 and may extend towards a center of the case insert 540. A proximal end of a hump may be towards an insert wall 542 and a distal end of a hump may be away from an insert wall 542.

The latitudinal insert humps 550 and the longitudinal insert humps 560 may be structured to have a height and width that allows for at least a portion of the electronic components positioned on an upper surface of the PCB 600 to be positioned within a corresponding hump. The width and height of the humps may also be structured so as to assist with the proper positioning of a dental appliance being stored within the dental appliance case 500. Various surfaces of the humps may be sloped or straight. For example, some surfaces of the latitudinal insert humper 550 may be sloped so as to aid in the proper positioning of the dental appliance with the dental appliance case 500.

The latitudinal insert humps 550 may comprise a plurality of latitudinal sensor apertures 556. In some embodiments, the latitudinal sensor apertures 556 are positioned towards a distal end of the latitudinal insert hump 550, although the apertures may be positioned at other locations along the latitudinal insert hump 550 in other embodiments. The latitudinal sensor apertures 556 may be positioned to correspond to a sensor, or portion thereof, located within the latitudinal insert hump 550. The latitudinal sensor apertures 556 may be further positioned so as to align with sensor apertures located on other humps. For instance, if a latitudinal insert hump 550 comprises three latitudinal sensor apertures 556 at a distal end, then the middle latitudinal sensor aperture 556 may be positioned to align with a latitudinal sensor aperture 556 of another latitudinal insert hump 550. However, the side latitudinal sensor apertures 556 may each be aligned with a longitudinal sensor aperture 566 positioned within the longitudinal insert hump 560.

By using a plurality of sensors with corresponding sensor apertures, more accurate determinations of adherence to aspects of a dental treatment plan may be made. This may even be the case when the sensors are configured to collect data corresponding to essentially the same aspect of the dental treatment plan. For instance, the sensors may be configured to detect the presence of the dental appliance, thereby providing data as to the adherence of the wear time aspect of a dental treatment plan. By utilizing the three sensors, a more accurate determination of the presence of the dental appliance within the dental appliance case 500 may be made.

For instance, it has been discovered that in some situations the data provided by a single occupancy sensor may not be sufficient to allow for an accurate and consistent determination of the presence of a dental appliance within the dental appliance case 500. This may partly be due to the positioning of the dental appliance within the dental appliance case 500. In certain positions, the dental appliance may disrupt the reception of the transmission sent by a part of a sensor such that an accurate determination may not be made. For example, the portion of the dental appliance through which the sensor transmission is being sent may not sufficiently absorb or reflect the sensor transmission, thereby providing enough of the transmission to the sensor receiver that a determination of non-occupancy is made. However, if multiple sensors are being used, sensor transmissions can be directed at different portions of the dental appliance. By directing transmissions at different portions of the dental appliance, there is a reduced possibility that an inaccurate determination will be made.

The latitudinal insert humps 550 may further comprise one of more latitudinal insert mounting aperture 554. The latitudinal insert mounting aperture may extend from an inner surface of the latitudinal insert hump 550 and extend essentially the height of the latitudinal insert hump 550. The latitudinal insert mounting aperture 554 may be positioned so as to align with the base mounting aperture 520. Mounting hardware may be used to secure the relative positioning of the base 510 and the case insert 540.

The longitudinal insert humps 560 may have a different length and width than the latitudinal insert humps 550. This may be partly due to different electronic components being positioned within the longitudinal insert humps 560 than in the latitudinal insert humps 550, although there may be some overlap in the types of electronic components located within each of the humps, for example parts of sensors. In some embodiments, the longitudinal insert humps 560 may have a flared width towards the proximal end and may have a tapered end towards a distal end. The differing widths of the longitudinal insert humps 560 may allow for differing sizes and types of electronic components to be positioned within the longitudinal insert humps 560.

The longitudinal insert humps 560 may comprise one or more longitudinal hump wall 562. The longitudinal hump wall 562 may be perpendicular or sloped compared to the floor of the case insert 540. The angle of the longitudinal hump wall 562 may depend on whether it is to be used to aid in the vertical positioning of the dental appliance within the dental appliance case 500. If the longitudinal hump wall 562 is to aid in the vertical positioning, then it may have a sloped angle. However, if the longitudinal hump wall 562 is to mainly assist with the horizontal positioning of the dental appliance, then the angle may be perpendicular.

One or more of the longitudinal insert humps 560 may comprise a longitudinal insert mounting aperture 564. The longitudinal insert mounting aperture 564 may be structured to extend from an inner surface of the longitudinal insert hump 560, and may extend for essentially the height of the longitudinal insert hump 560. The longitudinal insert mounting aperture 564 may be positioned so as to align with a base mounting aperture 520. Mounting hardware may be used to pass through the base mounting aperture 520 and into the longitudinal insert mounting aperture 564 so as to secure the relative position of the base 510 and the case insert 540.

One or more of the longitudinal insert humps 560 may comprise a separating wall 570. The separating wall 570 may extend from a distal end of the longitudinal insert hump 560. The separating wall 570 may extend towards the center of the case insert 540, but not so far as to block the sensor transmission between the two latitudinal insert humps 550. However, the separating wall 570 may extend so as to block at least a portion of the sensor transmission exiting a latitudinal sensor aperture 556 other than the latitudinal sensor aperture 556 aligned with the latitudinal sensor aperture 556 of the other latitudinal insert hump 550. An edge of the separating wall 570 may be sloped towards the center of the case insert 540. The relative positioning and shape of the separating wall 570 may aid in obtaining more suitable data for improving determinations of various aspects of the dental treatment plan. For example, the separating wall 570 may prevent interference from one sensor pair on another sensor pair. More specifically, the separating wall 570 may aid in blocking the sensor transmission exiting a center latitudinal sensor aperture 556 from being received by a side latitudinal sensor aperture 556 or a non-aligned longitudinal sensor aperture 566.

Figure 12A:
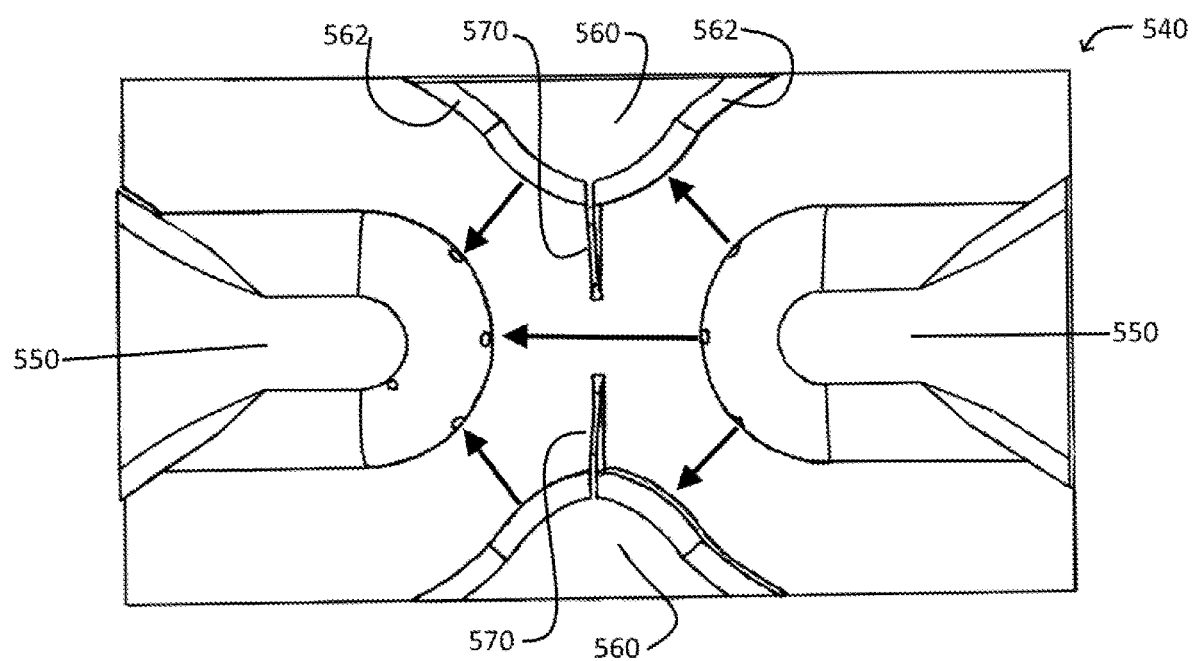
FIG. 12A, FIG. 12B, and FIG. 12C depict a top view of an embodiment of a case insert with embodiments of sensor transmission directions.

FIG. 12A depicts a top view of an embodiment of a case insert 540 with an embodiment of sensor transmission directions. In some embodiments, the sensors, or portions thereof, in the various humps may be arranged so as to further reduce interference. For instance, if the sensors are separated into a sensor transmitter and sensor receiver, the arrangement of these parts may aid in reducing interference. In some embodiments, sensor transmitters may be positioned within one of the latitudinal insert humps 550, while sensor receivers are arranged in the other latitudinal insert hump 550. However, the separating walls 570 may act to at least partially block the transmission from the side sensor transmitters being received by the side sensor receivers. Accordingly, the separating walls 570 may aid in preventing interference from non-aligned sensor transmitters. The non-aligned sensor transmitters and receivers may be aligned with corresponding sensor transmitters and receivers housed in the longitudinal insert humps 560. The general transmission direction of the sensor transmitters in this embodiment is depicted by the arrows in FIG. 12A.

Figure 12B:
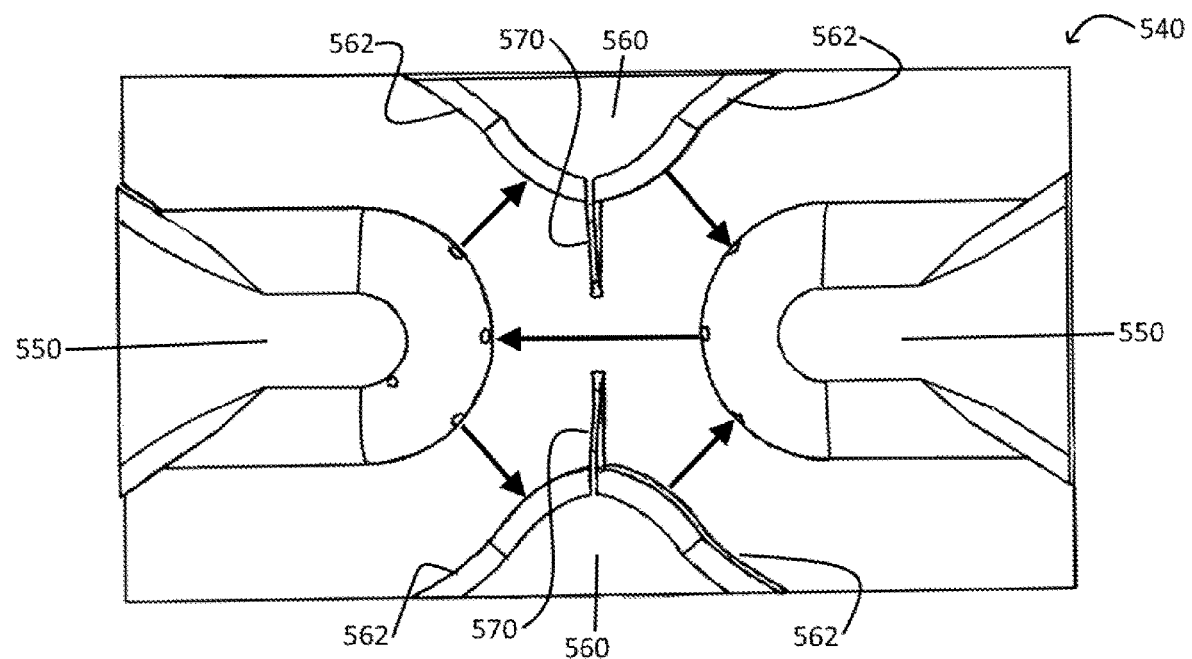

FIG. 12B depicts a top view of an embodiment of a case insert 540 with an embodiment of sensor transmission directions. In some embodiments, one of the latitudinal insert humps 550 may house one sensor transmitter and two sensor receivers, while the other latitudinal insert hump 550 may house one sensor receiver and two sensor transmitters. The corresponding sensor transmitters and sensor receivers that are not aligned between the latitudinal insert humps 550 may be aligned between the latitudinal insert hump 550 and the longitudinal insert hump 560. As the latitudinal insert hump 550 opposing the latitudinal insert hump 550 housing a single sensor transmitter only houses a single sensor receiver, there is a reduced probability that the transmission from the single sensor transmitter will interfere with the non-aligned sensor receivers. For example, the transmission from the single sensor transmitter will be at least partially blocked by the separating wall 570, thereby reducing the reception by the sensor receivers located in the longitudinal insert humps 560. Further, the separating walls 570 may aid in blocking the transmissions from the two sensor transmitters located in one of the latitudinal insert humps 550 being received by the two sensor receivers located in the opposing latitudinal insert hump 550. The general transmission direction of the sensor transmitters in this embodiment is depicted by the arrows in FIG. 12B.

Figure 12C:
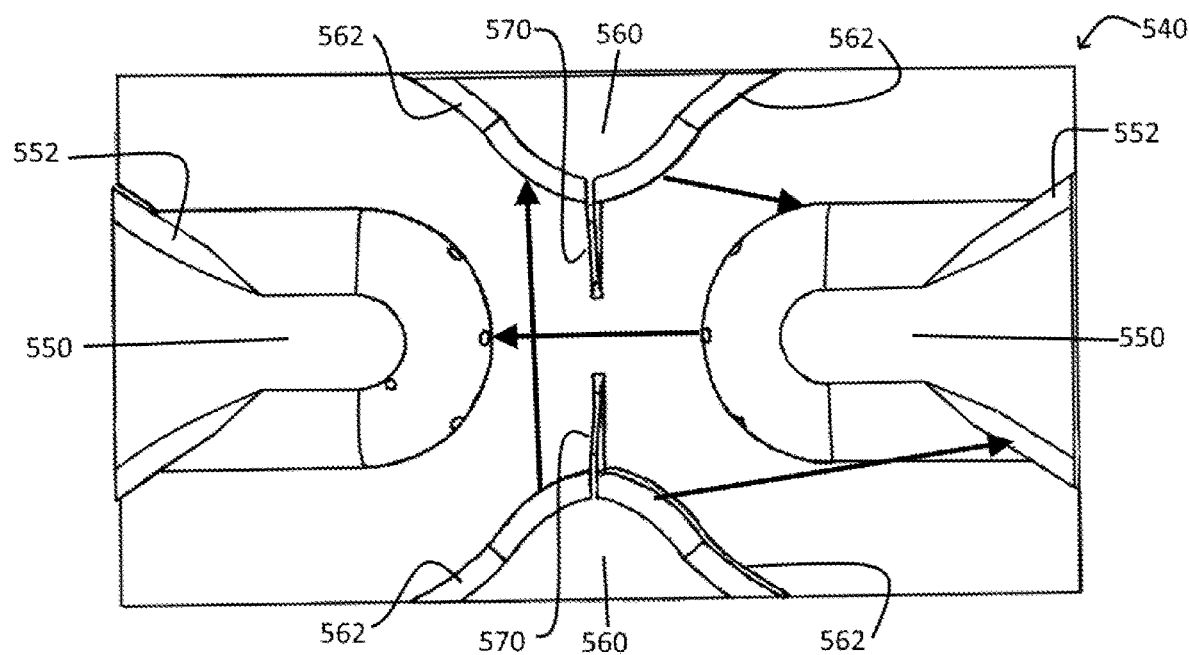

In some embodiments, the longitudinal insert humps 560 may be positioned so as to reduce interference from non-aligned sensor transmitters without utilizing a separating wall 570. For instance, the longitudinal insert humps 560 may extend further towards the center of the dental appliance case 500, and in some embodiments may be touch or merge the opposing longitudinal insert hump 560. By further extending towards a center of the dental appliance case 500, the sensors located within the longitudinal insert humps 560 may be positioned in locations that are more favorable for collecting data that result in more accurate and consistent determinations. For example, the sensors in the longitudinal insert humps 560 may be positioned such that the alignment of the sensors through the stored dental appliance is not perpendicular to the dental appliance. With such non-perpendicular alignment, there may be a lower probability that the sensor transmission will pass through the dental appliance without resulting in the anticipated transmissivity. The general transmission direction of the sensor transmitters in this embodiment is depicted by the arrows in FIG. 12C.

Figure 13:
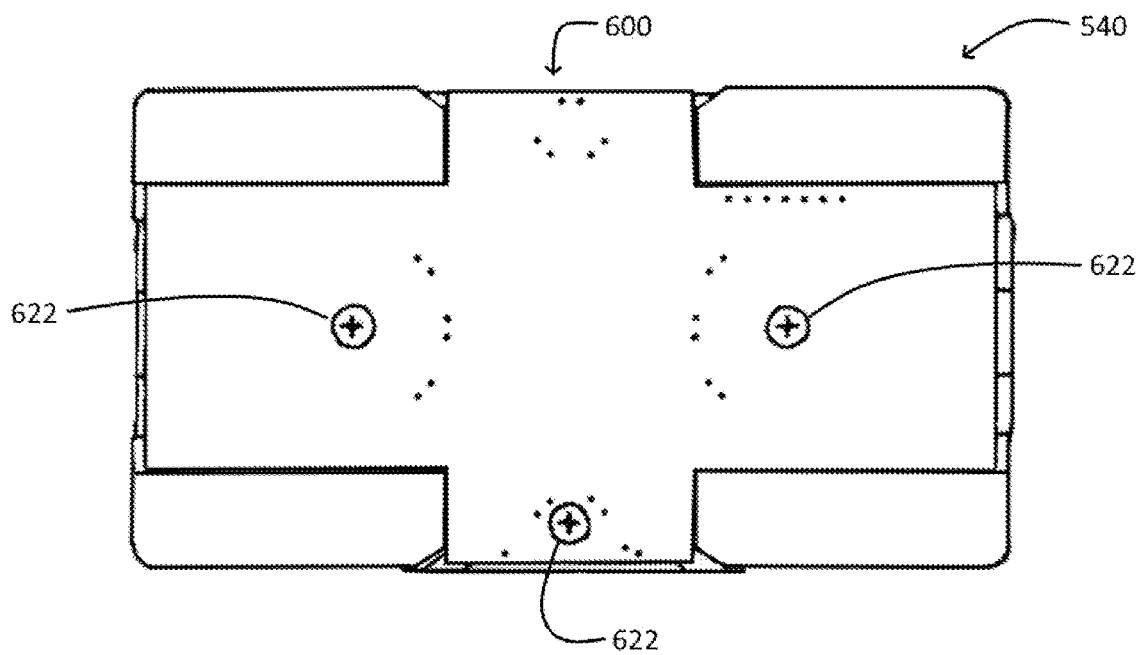
FIG. 13 depicts a bottom perspective view of an embodiment of a case insert mated with a PCB.

FIG. 13 depicts a bottom perspective view of an embodiment of a case insert mated with a PCB. The PCB 600 is positioned to fit within an insert PCB recess 544 and be held in relative position by the mounting hardware 622. Although this particular embodiment depicts the mounting hardware 622 contacting a lower surface of the PCB 600, other embodiment may have different configurations of the mounting hardware 622. In some embodiments, the insert PCB recess 544 may assist with aligning and securing the PCB 600 with respect to the case inert 540. The insert PCB recess 544 is formed in a bottom surface of a floor of the case insert 540. When the PCB 600 is positioned in the insert PCB recess 544, the lower surface of the PCB may be essentially aligned with the lower surface of the case insert 540, for example the lower surfaces may be essentially aligned along a single plane.

Figure 14:
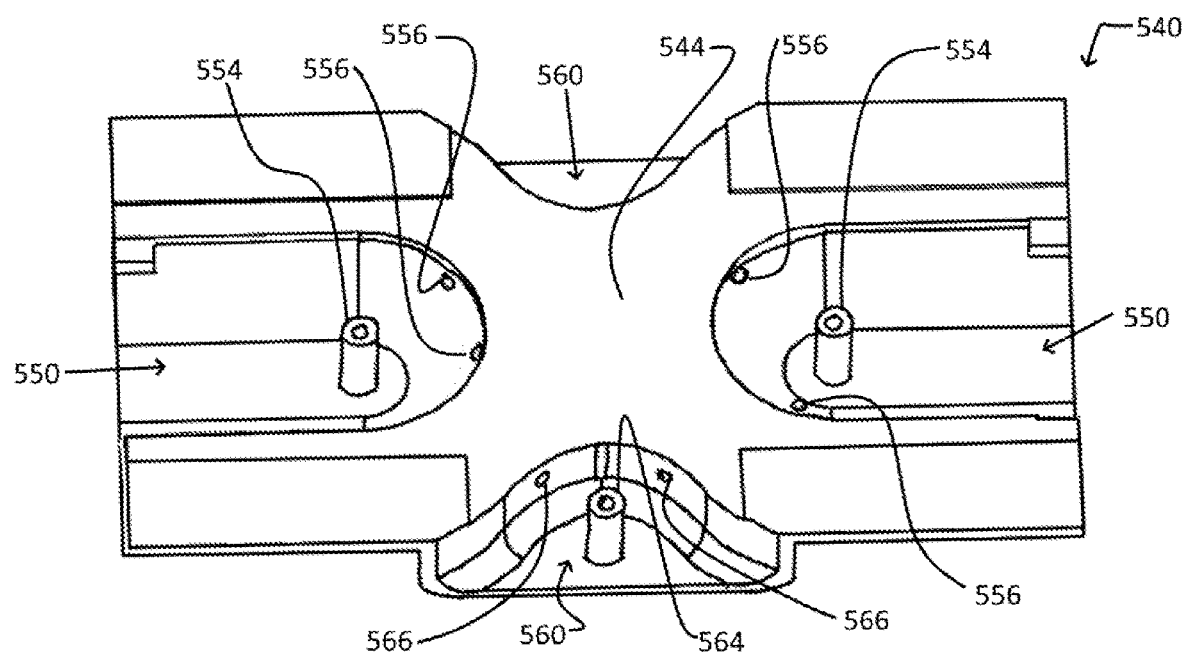
FIG. 14 depicts a bottom perspective view of an embodiment of a case insert of a dental appliance case.
Figure 15:
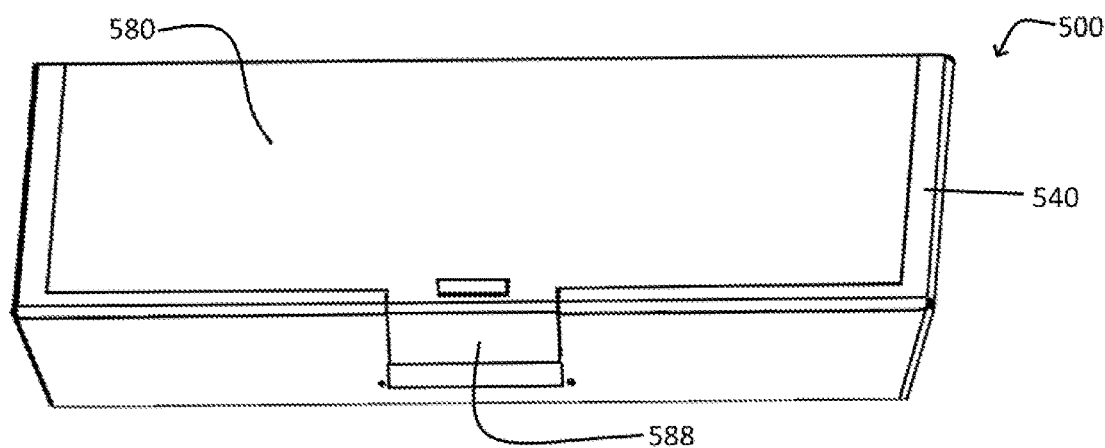
FIG. 15 depicts a top perspective view of an embodiment of a lid of a dental appliance case.

FIG. 14 depicts a bottom perspective view of an embodiment of a case insert. In this embodiment, the insert PCB recess 544 generally has an x-shape. More specifically, the insert PCB recess 544 may generally have a similar shape as the PCB, except for the areas corresponding to the latitudinal insert humps 550 and the longitudinal insert humps 560. However, the shape of the recess may depend on the shape of the PCB 600, and/or the arrangement of the electronic components positioned on the top surface of the PCB 600, and/or the presence/position of insert humps. For instance, if the case insert 540 comprises a single longitudinal insert hump 540, the PCB 600 may generally have a t-shape. In order to properly position and secure the PCB 600 with the case insert 540, the insert PCB recess 544 may generally also generally have a t-shape, except for the areas corresponding to the present latitudinal and longitudinal insert humps 550, 560.

In some embodiments, the case insert 540 comprises three mounting apertures, for example two latitudinal insert mounting apertures 554 and a single longitudinal insert mounting aperture 564. With the presence of three insert mounting apertures, the PCB 600 may be more properly aligned and sit more flush within the insert PCB recess 544. Additionally, as there are three points of contact with the other components being held together by the mounting hardware, there is a lower probability that the PCB 600 will be loose within the dental appliance case, such as due to manufacturing tolerances or warpage of the PCB 600.

However, in some embodiments, there may be less than three case mounting apertures. For example, only a pair of latitudinal insert mounting apertures 554 or only a pair of longitudinal insert mounting apertures 564 may be present. In other embodiments, none of the insert mounting apertures may be present. In such a situation, the PCB 600 may be directly adhered to the case insert 540 or the base 510. By reducing the number of insert mounting apertures, the overall size of the dental appliance case 500 may be reduced. More specifically, since area on the PCB 600 is not occupied by the presence of one or more PCB mounting aperture 622, the electronic components positioned on the top of the PCB 600 may be placed more closely together. Accordingly, the size of the PCB 600, case insert 540, and dental appliance case 500 may be smaller.

One of the benefits of positioning at least a part of a sensor in one or more latitudinal insert hump 550 and at least a part of a sensor in one or more longitudinal insert hump 560 is that the arrangement allows for detection of separate dental appliances. For instance, since sensor pairs are positioned so as to primarily obtain data corresponding to separate dental appliances. For example, some of the sensor apertures depicted in the embodiment of FIG. 11 are aligned between the latitudinal insert humps 550 and the longitudinal insert humps 560. As each dental appliance is positioned within the case, these aligned sensor pairs would be positioned so as to detect aspect(s) of a dental treatment plan corresponding to only one of the stored dental appliances.

However, in some embodiments, although the dental appliance case 500 may be able to separately detect aspect(s) of a dental treatment plan corresponding to only a single dental appliance, the dental appliance case 500 may not be configured to determine which dental appliance data is being gathered for. Accordingly, it may be desirable in some embodiments to select sensor(s) or position the sensor(s) so that the gathered data may be used to determine which dental appliance for which data is being gathered.

In some embodiments, differing features of separate dental appliances may be used for determining which dental appliance data is being gathered. For example, the thickness of a dental appliance structured for a patient's upper row of teeth may be different than the thickness of a dental appliance structured for a patient's lower row of teeth. In such a situation, the differing anticipated sensor readings could be used for determining which dental appliance data is being gather. As another example, one of the dental appliances may have a structural feather that is not present in the other dental appliance case. In such a situation, the differing structural feature could be detected by one or more sensor, thereby providing the data necessary for determining which dental appliance data is being gathered.

One of the benefits of determining which dental appliance data is being gathered, is that it allows for more accurate data gathering for determining adherence to aspects of a dental treatment plan and allows for better customizability of the dental treatment plan, or any updates that may be needed thereof. Additionally, fewer sensors may be necessary within the dental appliance case 500. For instance, independently gathering data for each dental appliance may make it such that the middle sensor pair within the latitudinal insert humps of FIG. 11 is not needed.

In some embodiments, the PCB 600 may be split into multiple PCBs. The sections of the split PCB may be electrically connected via known methods, such as a ribbon cable or when brought into contact, but may alternatively function independent of one another. That is, each of the sections of the split PCB may independently communicate with an external client.

If a split PCB is implemented, the base 510, case insert 640, and/or lid 580 may also be structured to be split into multiple sections. One or more section of the base 510, case insert 640, and/or case insert 640 may be connected to a corresponding section by a hinge. In such a configuration, at least one section of the split PCB may be positioned in a section of the split case insert that is different from the positioning of the other section(s) of the split PCB. One of the benefits of implementing split components is that it allows the patient to fold the dental appliance case 500 for more convenient storage. In some configurations, it also allows the user to selectively choose whether to fold the dental appliance case 500, or keep it unfolded, thereby aiding in adapting to differing storage situations.

Figure 16:
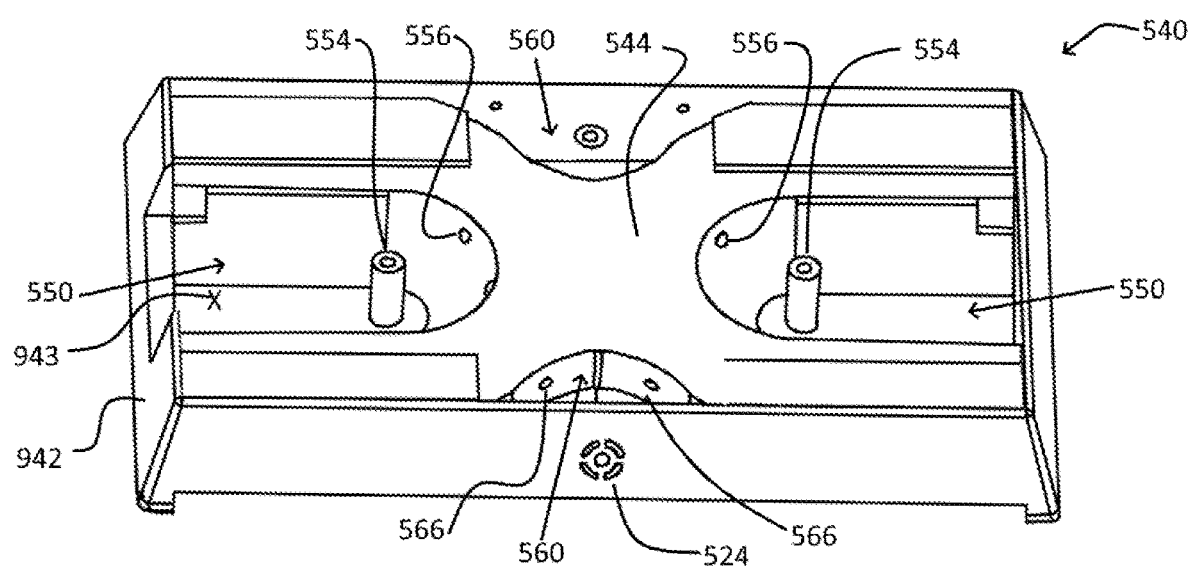
FIG. 16 depicts a bottom perspective view of an embodiment of a case insert of a dental appliance case.
Figure 17:
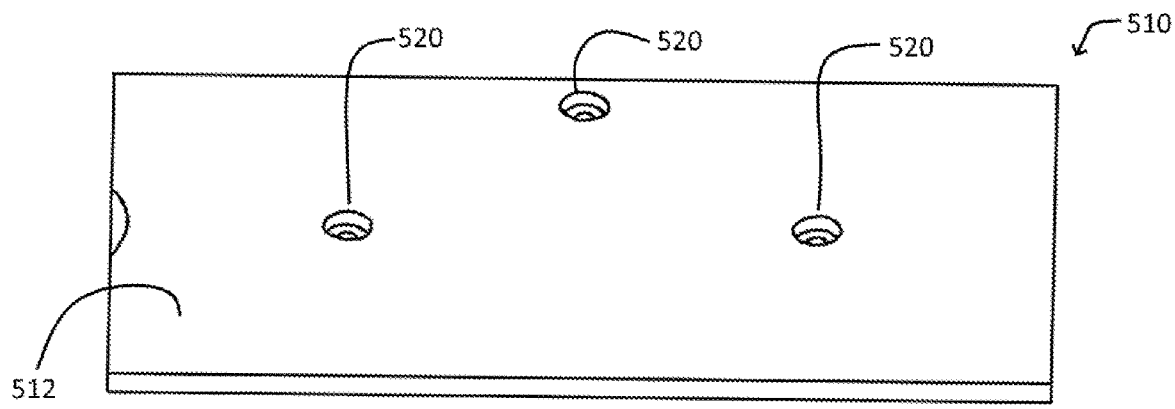
FIG. 17 depicts a bottom perspective view of an embodiment of a base of a dental appliance case.

FIG. 16 depicts a bottom perspective view of an embodiment of a case insert 540 of a dental appliance case 500. FIG. 17 depicts a bottom perspective view of an embodiment of a base 510 of a dental appliance case 500. In some embodiments, the base wall 514 may be substantially reduced in size, or be non-existent. In such embodiments, the insert wall 542 may be structured to extend below the floor of the case insert 540. The insert wall 542 may extend to such an extent as would be necessary to substantially house the PCB 600. The base 510 may be positioned below the PCB 600. The case insert 540, PCB 600, and the base 510 may be held in relative positioning by the mounting hardware 622, as previously described. The base 510 may comprise one or more cavity for at least partially housing an electronic component electrically connected to the PCB 600. One of the benefits of reducing or removing the base wall 514 is that it allows for an overall reduction in the size of the dental appliance case 500.

Figure 18:
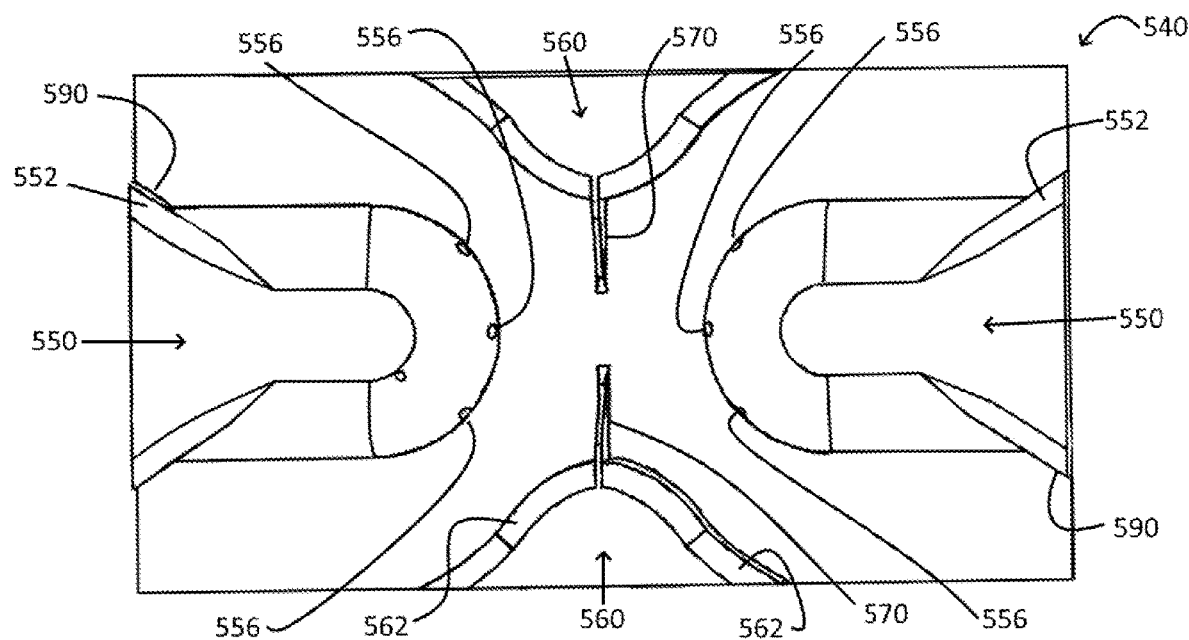
FIG. 18 depicts a top view of a case insert of a dental appliance case.
Figure 19:
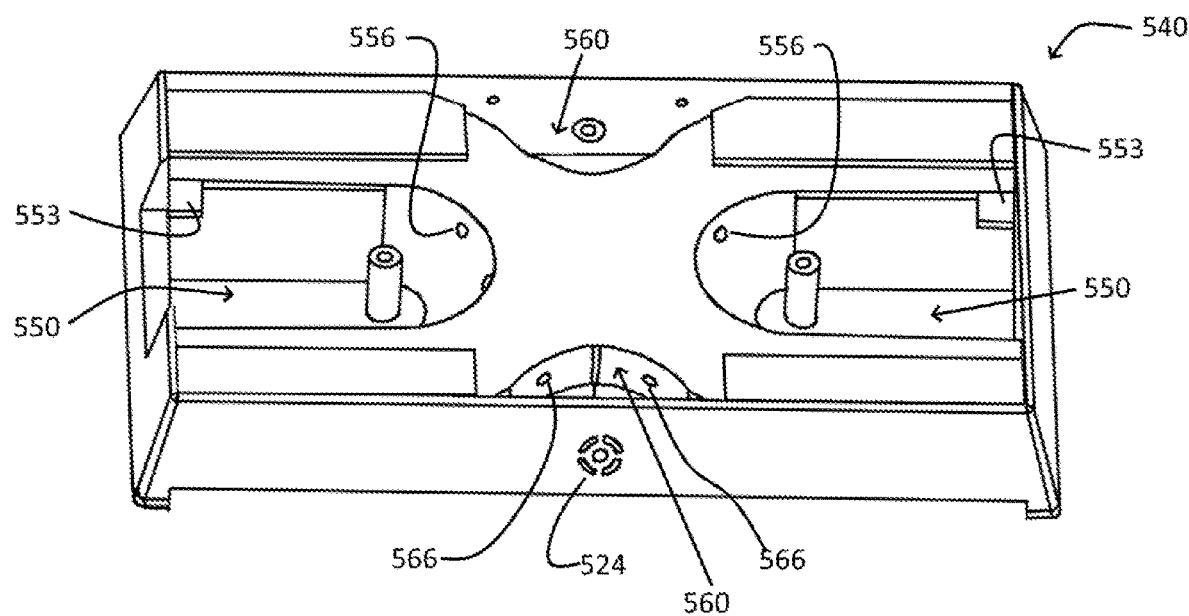
FIG. 19 depicts a bottom perspective view of a case insert of a dental appliance case.

FIGS. 18 and 19 depict perspective views of an embodiment of a case insert. In this and similar embodiments, the case insert 540 further comprises a latitudinal hump flare 552. The top surface of the latitudinal hump flare 552 may be aligned with the top surface of the latitudinal insert hump 550 or may be positioned to be higher than the top surface of the latitudinal insert hump 550. The side surfaces of the latitudinal hump flare 552 may be positioned to be above the side surfaces of the latitudinal insert hump 550. The side surfaces of the latitudinal hump flare 552 may be structured to be misaligned with the side surfaces of the latitudinal insert hump 550, such that they are non-parallel. The slope of the latitudinal hump flare 590 may be steeper than the slope of the side surfaces of corresponding side surfaces of the latitudinal insert hump 550.

The latitudinal hump flares 552 may further comprise one or more flare cavity 553. The flare cavity 553 may be positioned on an under side of the case insert 540 such that it is positioned deeper than the inside side surface of the latitudinal insert hump 550 and in an area corresponding to the latitudinal hump flare 552. The depth of the flare cavity 553 may differ in different embodiments. However, it is preferable that the depth is such that it allows for housing a portion of an electronic component electrically connected to the PCB 600. As such, one of the benefits of the flare cavity 553 is that it allows for positioning portions of larger electronic components, without compromising the overall aesthetics and dental appliance positioning capabilities of the latitudinal insert hump 550.

Figure 20:
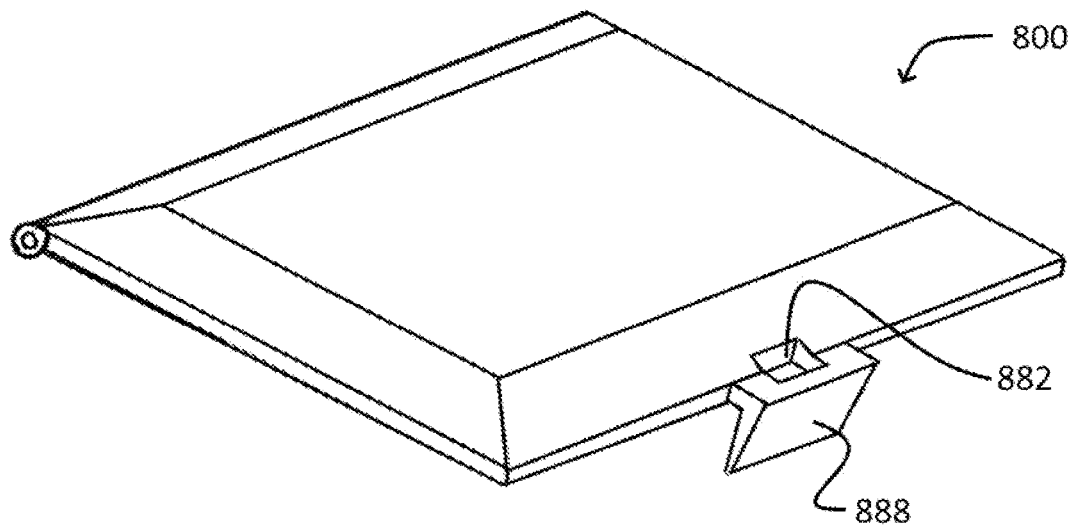
FIG. 20 depicts a top perspective view of a lid of a dental appliance case.

FIG. 20 depicts a perspective view of an embodiment of a lid 880 of a dental appliance case. In this and similar embodiments. The lid 880 comprises a lid locking mechanism 888. The lid locking mechanism 888 may be structured and positioned such that it may engage a portion of a case insert wall and be positioned to be between portions of a base wall, if present. The lid locking mechanism 888 is configured to engage a portion of the case insert in order to keep the lid 880 and the base in relative position such that the lid covers the cavity formed by the case insert. The locking mechanism 888 may be temporarily disengaged with the portion of the case insert such that the lid 880 may be opened to allow for access to the cavity formed by the case insert.

The lid 880 may further comprise a lid aperture 882. The lid aperture may be positioned so as to align with the lid locking mechanism 888. The lid aperture 882 may be structured to allow for greater movement of the lid locking mechanism 888 when engaging and disengaging from the case insert.

In some embodiments, the dental appliance case may further comprise a battery tray 990. The battery tray 990 may comprise a tray wall 992 and a battery cavity 994. The tray wall 992 may be positioned towards one or more sides of the battery cavity 994. The tray wall 992 may be structured so as to fit within a cavity formed by an insert wall opening 943 formed in an insert wall 942. When a surface of the tray wall 992 is aligned with a surface of the insert wall 942, the battery cavity 994 may be structured so as to extend within a cavity formed by the case insert and/or a latitudinal insert hump. The battery cavity 994 may further be structured so as to be positioned towards one side of the PCB, for example an upper side, and to at least engage a component attached to the PCB and/or the inner surface of a portion of the case insert, such as the inner surface of the latitudinal insert hump. The battery cavity 994 may be structured so as to receive and partially secure a power source, such as a coin battery. The battery cavity 994 may be structured so as to partially secure the power source within the battery cavity 994 to allow a user to insert, remove, and/or replace the power source within the case insert.

The battery tray 990 may further comprise a tray locking mechanism 996. The tray locking mechanism may contact a portion of the case insert so as to maintain the battery tray 990 is a relative position to the case insert.

What is claimed is:

1. A medical device storage case, comprising:
   a base;
   a case insert connected to the base;
   an insert hump connected to the case insert and structured to position a medical device within a cavity at least partially formed by the case insert;
   at least a portion of a sensor located within the insert hump and configured to detect a feature of the medical device, wherein:
   a width of a distal end of the insert hump is smaller than a width of a proximal end of the insert hump.

2. The medical device storage case of claim 1, wherein the feature of the medical device is the presence and/or absence of the medical device within the cavity.

3. The medical device storage case of claim 1, wherein the insert hump primarily extends from a wall of the case insert towards an opposite wall of the case insert.

4. The medical device storage case of claim 3, wherein the distal end of the insert hump is spaced apart from the opposite wall of the case insert.

5. The medical device storage case of claim 1, wherein a height of the distal end of the insert hump is lower than a height of the proximal end of the insert hump.

6. The medical device storage case of claim 1, wherein the portion of the sensor is located within the distal end of the insert hump.

7. The medical device storage case of claim 6, further comprising an electronic component having a height greater than the portion of the sensor, the electronic component being located within the proximal end of the insert hump.

8. The medical device storage case of claim 1, wherein the case insert comprises a side wall that extends below a floor of the case insert.

9. A medical device storage case, comprising:
   a base;
   a case insert connected to the base;
   a first latitudinal insert hump connected to the case insert;
   a second latitudinal insert hump connected to the case insert; and
   a first portion of a sensor located within the first latitudinal insert hump and a second portion of the sensor located within the second latitudinal insert hump, the portions of the sensor being configured to detect a feature of a medical device positioned between the first and second latitudinal insert humps.

10. The medical device storage case of claim 9, wherein distal ends of the first and second latitudinal insert humps face each other across a center axis of the case insert.

11. The medical device storage case of claim 10, wherein:
    each of the distal ends of the first and second latitudinal insert humps comprise a sensor aperture, and
    the sensor apertures are aligned with each other across the center axis of the case insert.

12. The medical device storage case of claim 9, further comprising:
    a first longitudinal insert hump connected to the case insert; and
    a second longitudinal insert hump connected to the case insert.

13. The medical device storage case of claim 12, wherein:
    distal ends of the first and second longitudinal humps face each other across a center axis of the case insert, and
    the distal ends of the first and second longitudinal humps do not face a distal end of the first or second latitudinal insert hump.

14. The medical device storage case of claim 12, wherein a distal end of each of the first and second longitudinal insert humps comprise a sensor aperture aligned with a sensor aperture located within a distal end of the first or second latitudinal insert hump.

15. The medical device storage case of claim 12, wherein a portion of a sensor is located within at least one of the first and second longitudinal insert humps.

16. The medical device storage case of claim 12, further comprising a separating wall extending from a distal end of the first longitudinal hump.

17. The medical device storage case of claim 16, wherein the separating wall is located between two sensor apertures positioned at the distal end of the first longitudinal hump.

18. The medical device storage case of claim 12, wherein:
   distal ends of the first and second longitudinal humps extend towards each other, and
   distal ends of the first and second latitudinal humps extend towards each other.

19. The medical device storage case of claim 18, wherein the distal ends of the first and second longitudinal humps do not extend in the same direction the distal ends of the first and second latitudinal humps extend.

* * * * *